(12) United States Patent
Knifton et al.

(10) Patent No.: US 6,191,310 B1
(45) Date of Patent: *Feb. 20, 2001

(54) DIAMINOALKANE SYNTHESES VIA SELECTIVE AMINATION OF DIHYDRIC ALCOHOLS

(75) Inventors: John Frederik Knifton; Daniel John Janitor, both of Houston, TX (US)

(73) Assignee: Shell Oil Company, Houston, TX (US)

( * ) Notice: This patent issued on a continued prosecution application filed under 37 CFR 1.53(d), and is subject to the twenty year patent term provisions of 35 U.S.C. 154(a)(2).

Under 35 U.S.C. 154(b), the term of this patent shall be extended for 0 days.

(21) Appl. No.: 09/442,235

(22) Filed: Nov. 17, 1999

Related U.S. Application Data

(60) Provisional application No. 60/109,559, filed on Nov. 23, 1998.

(51) Int. Cl.$^7$ ............................................. C07C 209/00
(52) U.S. Cl. .............................. 564/479; 564/480
(58) Field of Search ..................... 564/479, 480

(56) References Cited

U.S. PATENT DOCUMENTS

| | | | |
|---|---|---|---|
| 3,270,059 | 8/1966 | Winderl et al. | 260/583 |
| 3,520,933 | 7/1970 | Adam et al. | 260/585 |
| 4,152,353 | 5/1979 | Habermann | 260/585 B |
| 4,153,581 | 5/1979 | Habermann | 252/472 |
| 4,409,399 | 10/1983 | Swift et al. | 564/473 |
| 4,622,428 | 11/1986 | Merger et al. | |
| 4,683,336 | 7/1987 | Blackhurst | 564/480 |
| 4,806,690 | 2/1989 | Bowman | 564/480 |

OTHER PUBLICATIONS

Josef Pašek et al, "Equilibrium Conditions for Amination of Alcohols and Carbonyl Compounds," *Ind. Eng. Chem. Prod. Res. Develop.,* 11, 3, 333–337 (1972). Month unavailable.

Alfons Baiker et al., "Catalytic Amination of Long Chain Aliphatic Alcohols," *Ind. Eng. Chem., Prod. Res. Dev.,* 16, 3, 261–266 (1977). Month unavailable.

Michael E. Ford et al., Selective Catalytic Synthesis of Mixed Alkylamines and Polyfunctional Amines, *Catalysis of Organic Reactions,* D. W. Blackburn, ed., Ch. 14, pp. 219–240 (1990) month unavailable.

J. F. Knifton and D. J. Janitor, "Diaminoalkane Syntheses Via Selective Amination of Hydroxy Aldehydes," Patent Application Serial No. 60/109,572, filed Nov. 23, 1998 (Docket No. TH–1160).

*Primary Examiner*—Samuel Barts

(57) ABSTRACT

Disclosed is a process for selectively producing diaminoalkanes which comprises reacting a dihydric alcohol characterized by two to six carbons, preferably 1,3-propanediol, with excess ammonia and sufficient hydrogen to stabilize a nickel or cobalt-containing hydroamination catalyst, at a temperature of at least 150° C. and a pressure of at least 500 psig, until there is substantial formation of the desired diaminoalkane, wherein said catalyst comprises at least one metal selected from the group consisting of nickel and cobalt, or mixtures thereof, optionally in the presence of one or more promoters, but particularly molybdenum oxide.

30 Claims, No Drawings

DIAMINOALKANE SYNTHESES VIA SELECTIVE AMINATION OF DIHYDRIC ALCOHOLS

CROSS-REFERENCE

This application claims the benefit of U.S. Provisional Application No. 60/109,559, filed Nov. 23, 1998, the entire disclosure of which is hereby incorporated by reference.

This application is related to U. S. patent application Ser. No. 60/109,572, filed of even date and incorporated by reference herein in its entirety).

FIELD OF THE INVENTION

This invention relates to hydroamination. In particular this invention is related to a process for the selective hydroamination of a hydrocarbon having from two to six carbons and characterized by two hydroxy groups, preferably separated by at least one or more carbons to yield a diaminoalkane. The reactants would include diols having two to four carbons, and mixtures of same. Examples could include ethylene glycol, 1,2-propanediol, and 1,3-propanediol. In the preferred embodiment this invention provides a process for the selective hydroamination of 1,3-propanediol to yield 1,3-propanediamine and its homologues in one step. Greater than 95% conversions of 1,3-propanediol (PDO) and 38% effluent concentrations of 1,3-propanediamine (PDA) are demonstrated per pass.

BACKGROUND

The hydroamination of commodity and specialty alcohols, aldehydes and ketones to manufacture the corresponding aliphatic amines is known in the art. The selection of a catalyst with optimal advantages has also been the focus of much research. Aliphatic amines are of considerable industrial importance and find applications in many facets of modern technology, agriculture and medicine. Lower aliphatic amines ($C_1$ to $C_6$) are particularly important for both the chemical and pharmaceutical industries.

In an article titled "Equilibrium Conditions for Amination of Alcohols and Carbonyl Compounds", *Ind. Eng. Chem. Prod. Res. Develop.*, 11, 3, 333–337 (1972), Josef Pasek et al. described the influence of pressure, temperature, and initial composition on the equilibrium content of primary, secondary, and tertiary amines and unsaturated compounds.

Alfons Baiker et al., in an article titled "Catalytic Amination of Long Chain Aliphatic Alcohols", *Ind. Eng. Chem., Prod. Res. Dev.*, 16, 3, 261–266 (1977), indicate a preference for the use of a copper catalyst in the amination of dodecanol with dimethylamine.

In *Catalysis of Organic Reactions*, Blackburn, D. W., ed., 1990, at Chapter 14, M. Ford et al. review the selective synthesis of mixed alkyl amines by amine-alcohol reactions over hydrogen phosphate.

The amination of alcohols, aldehydes, and ketones using catalysts containing nickel, copper, or both, has been also been described, for example, in U.S. Pat. Nos. 3,520,933; 4,153,581; 4,152,353; and 4,409,399. These patents do not appear to contemplate the selective production of diamines.

The process disclosed in U.S. Pat. No. 4,683,336 employs catalysts comprising carbonates of copper, nickel, and cobalt, or mixtures thereof to produce amines from aliphatic alcohols or aliphatic aldehydes.

U.S. Pat. No. 4,806,690 discloses a method of preparing amines from an alcohol, aldehyde, ketone or mixture thereof, in the presence of a catalyst containing about 1 to 20% cobalt, 75 to 95% copper, 1 to 16% of a third component selected from iron, zinc, zirconium, and mixtures thereof. The preferred embodiment demonstrates the reductive amination of MEA.

U.S. Pat. No. 3,270,059 discloses the production of diaminoalkanes by passing an alkanediol, alkanolamine, alkylene oxide, or alkyleneimine along with either ammonia or an alkylamine in the presence of hydrogen and at an elevated temperature over a catalyst which contains sintered cobalt or nickel. The sintering process requires extra steps and high temperatures.

From the foregoing references it appears there is a need in the art for an improved method of selectively producing shorter chain diaminoalkanes. There does not appear to be a disclosure of the amination a short chain diol, such as, for example, 1,3-propanediol to 1,3-propanediamine in one step with greater than 90% conversions of 1,3-propanediol per pass. It would be very desirable in the art if a process were available for aminating a diol which is available in large volumes. This would provide an attractive route to an added-value commodity chemical. These diamines could find large volume applications in polyamide resins as monomer/comonomers, as well as price-competitive usage in lube oils, epoxies, hot melt adhesives, and surfactants. They might also be useful in fuel additives, chelating agents, fungicides, and plastic lubricants.

SUMMARY

In accordance with the foregoing, there is disclosed a hydroamination process which comprises reacting a diol characterized by two to six carbons, preferably 1,3-propanediol with excess ammonia and sufficient hydrogen to stabilize a catalyst which comprises at least one metal selected from the group consisting of nickel and cobalt, or mixtures thereof, optionally supported, or as a bulk-metal catalyst, and optionally in the presence of one or more promoters, at a temperature of at least 150° C. and a pressure of at least 500 psig until there is substantial formation of the desired diaminoalkane. Said hydroamination exhibits good selectivity for the desired diaminoalkanes and may be conducted batchwise or in a continuous reactor system.

DETAILED DESCRIPTION OF THE INVENTION

In the broader aspect of this invention diaminoalkanes of two to six carbons are prepared in one step from a diol, preferably in a solvent, in the presence of excess ammonia and sufficient hydrogen to stabilize the catalyst, at a temperature of at least 150° C. and at a pressure of at least 500 psig, and separated, optionally, by fractional distillation.

The amination reaction of this invention to prepare diaminoalkanes from diols in the presence of ammonia and hydrogen in one step can be represented by the following general equation (Equation I):

(I)

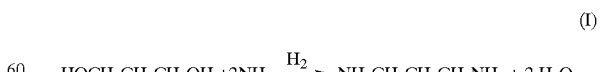

In Equation I using, for example, a Raney nickel catalyst containing 55% Ni+a Mo promoter, greater than 95% conversion of 1,3-propanediol has been demonstrated, and 1,3-propanediamine is obtained in ca. 38% yield at 200° C. The selective amination of 1,3-propanediol yields 1,3- propanediamine (1,3-PDA) and its homologues. The specific homologues include dipropylene triamine (DPTA) and tripropylene tetramine (TPTA). All three classes of amines were identified through a combination of gc and gc-ms/ir techniques.

The feedstock used in the practice of this invention comprises a diol having from two to six carbons, preferably separated by only one carbon, and mixtures of same. Examples may include ethylene glycol, 1,2-propanediol, 1,3-propanediol and 1,4-butanediol.

The process is particularly suited to the amination of 1,3-propanediol because of its properties. For example, it is soluble in a variety of alcohols, ethers, and water. Preferably, therefore, the 1,3-propanediol is fed into the amination reactor in a suitable solvent. Solvents may include water, and functionalized hydrocarbons having up to about twenty carbons per molecule, as well as mixtures thereof. Suitable solvents would include alcohols and ethers. They may include, for example, tert-butanol and methyl tert-butyl ether. Generally, primary and secondary alcohols would not be suitable. The preferred embodiment discloses the use of an aqueous solution of 1,3-propanediol. The amount of 1,3-propanediol in the aqueous solution may be from about one to about 90%, but the preferred range is from about 20 to 80% and the use of a 25% aqueous solution is demonstrated in the examples. In the preferred embodiment, a solution of about 25% aqueous 1,3-propanediol is fed into a continuous flow reactor.

In the one-step process of this invention, the reaction takes place in the presence of excess ammonia and sufficient hydrogen to stabilize the catalyst. The nitrogen source is required to be ammonia, preferably in gaseous form. The amination conditions to be utilized suitably include the use of from 5 to 200 moles of ammonia per hydroxyl equivalent of feedstock and from about 0.1 to about 100 mole equivalents of hydrogen per hydroxyl equivalent of feedstock.

A suitable catalyst comprises at least one Group VIII metal, optionally on a support. Promoters may also be used. Suitable metals include cobalt, nickel, copper, and molybdenum. Particularly effective catalyst compositions in accordance with the present invention are Raney nickel, Raney cobalt, supported and bulk-metal nickel or cobalt, as well as mixtures thereof, optionally with a one or more promoters. The preferred catalysts are Raney nickel and Raney cobalt, and bulk-metal nickel or cobalt catalysts. Raney nickel and Raney cobalt are catalysts manufactured by W. R. Grace & Co. Raney nickel catalysts are composed of nickel, plus optionally copper, chromium, and molybdenum and contain, on an oxide-free basis, from about 10 to 95 wt % nickel. Raney cobalt catalysts are composed of cobalt and nickel and, optionally, they also contain molybdenum. On an oxide-free basis they may comprise about 10 to 95% cobalt. Especially preferred is a Raney nickel or cobalt catalyst containing from about 50 to 60 wt % nickel or cobalt. Said catalysts may be in many different forms, particularly granules, extrudates, and powders.

In some examples the catalyst was used with one or more promoters. Suitable promoters include smaller amounts of one or more additional Group VIII metals, and metals from Group IB and VIB of the Periodic Table. This includes chromium, molybdenum, tungsten, and copper. The examples demonstrate that a Mo promoter seems to be particularly effective.

The catalyst may be on a support. Supports may be selected from Groups II, III, IV, or V of the Periodic Table. The preferred supports include magnesia, alumina, silica, zirconia, and titania, as well as mixtures thereof. Where a support is used, it is preferably alumina or silica.

Said catalyst may also be selected from bulk-metal catalysts prepared through coprecipitation of the different metal salts, as their carbonates, etc. The nickel or cobalt bulk-metal catalysts may also contain other metals as promoters, particularly copper, chromium, and molybdenum. The nickel or cobalt content of such bulk-metal catalysts is typically 10 to 95%. The preferred metal promoter is molybdenum, present as molybdenum oxide. Using a nickel bulk-metal oxide catalyst the preferred level of molybdenum oxide promoter is from 0.1 to 4 weight %. Said catalysts may be employed in many different forms, including tablets, extrudates, powders, etc.

The catalyst is preferably introduced into the reaction zone initially.

The temperature for the one-step process should be at least about 150° C. A suitable range is from about 150° C. to about 250° C. The preferred range is from about 160° C. to about 240° C., and a particularly preferred range for the one-step process is from about 180° C. to about 220° C. With 1,3-propanediol as the starting alkanol, hydroamination can be safely conducted at temperatures exceeding 200° C., without excessive secondary product formation.

The pressure should be at least about 500 psi. A suitable range is from about 500 psi to about 5000 psi. The preferred range is from about 1000 psi to about 3000 psi, and particularly preferred is from about 2000 to 2500 psi.

When the reaction is conducted on a continuous basis using the described nickel or cobalt catalysts liquid feed rates may range from about 0.1 to 5.0 LHSV. A preferred range is from about 0.4 to 2.0 LHSV.

The reaction mixture formed as a result of the hydroamination of the 1,3-propanediol may be recovered and fractionated in any suitable manner, such as by fractional distillation, to obtain unreacted feed components, by-products, and the desired 1,3-propanediamine.

The products have been identified in this work by one or more of the following analytical procedures; viz, gas-liquid chromatography (gc), infrared (ir), mass spectrometry (ms), or a combination of these techniques. All temperatures are in degrees centigrade and all pressures in pound per square inch (psi). The process of the invention can be conducted in a batch, semi-continuous, or continuous manner.

The examples which are discussed below were conducted in a 50 cc capacity, continuous reactor system operated in the liquid-full, plug-flow mode, and fitted with the appropriate controls. The feedstocks were aqueous, 25% 1,3-propanediol solutions unless otherwise specified. The PDO employed was a redistilled material.

The LHSV was varied from 0.16 to 1.0. The preferred hydroamination took place over a range of temperatures from about 180° C. to about 220° C.

In the one-step hydroamination, at a temperature of 180° C., 1,3-propanediol conversion levels are as high as 65%, and the typical effluent sample comprises about 10 to 32% 1,3-propanediamine (PDA) (ex.s 1, 2,4, 5, 6, and 8, basis gc analyses, FI detector) with dipropylenetriamine (DPTA) as a major coproduct in up to 7.2% yield.

At a temperature of 200° C., 1,3-propanediol conversion levels are as high as 90%, and the typical effluent sample comprises about 30 to 38% 1,3-propanediamine (ex. 1, 4, 5, 6, 8, 9, and 10). DPTA concentrations in these examples are as high as 12.1%.

At a temperature of 220° C., 1,3-propanediol conversions are as high as 97% (ex. 4), The typical effluent sample comprises about 29 to 36% 1,3-propanediamine (ex. 1, 3, 5, and 10). DPTA concentrations are as high as 10% (ex. 10).

In Example 1, Table 1, using a Raney cobalt catalyst with a Ni/Mo promoter, at 200° C., LHSV 1.0, there is a 75% conversion of 1,3-PDO and a 33% effluent concentration of 1,3-propanediamine is realized (by gc analyses using a Fl detector). With the same Raney cobalt catalyst, the 1,3-PDA plus DPTA selectivity is ca. 60%. 3-Amino-1-propanol (APO) makes up the majority of the remaining product, but some N-alkyl- and N,N-dialkyl-1,3-diaminopropanes have also been confirmed via gc-ms/ir analyses.

Particularly good results are demonstrated in Example 4, Table IV, where a conversion of 1,3-propanediol of greater than 95% per pass is demonstrated at 220° C. using a 55% nickel catalyst with a Mo promoter. In the same example, a 38% concentration of 1,3-propanediamine effluent is demonstrated at 200° C.

Table XII summarizes data relating to 1,3-PDA and DPTA selectivities, as well as 1,3-PDO conversion levels. As expected, lower feed rates tend to favor higher 1,3-propanediol conversion levels, lower 3-amino-1-propanol (APO) concentrations, and slightly elevated 1,3-propanediamine (PDA)+dipropylenetriamine (DPTA) selectivities. At lower temperatures, the 1,3-propanediamine+dipropylenetriamine selectivity may reach 62% when using the bulk-metal Ni catalyst of Example 6.

The selected catalysts include a Raney cobalt catalyst with nickel/molybdenum promoters (ex.1 and 2), a Raney nickel catalyst (ex. 3–5 and 10–11), and a bulk-metal nickel catalyst comprising 50% nickel and 1.8% molybdenum oxide (ex. 6, 8 and 9). Conversions of>80 wt % or more and high 1,3-DAP selectivities are obtainable with the process of the present invention, such that only trace quantities of unreacted feedstock and lesser amounts of DPTA, TPTA, PDO etc. co-products are present in the reaction mixture.

The 1,3-PDA, DPTA, TPTA products were separated by fractional distillation and identified through a combination of gc and gc-ms/ir techniques. Smaller quantities of 1-amino-3-propanol, and N-alkylated diamines, such as N,N-dimethyl-1,3-diaminopropane, N-propyl-1,3-diaminopropane, and N-ethyl-1,3-diaminopropane were also confirmed via gc-ms/ir, together with 1,3-PDO and 2(2-hydroxyethyl)-1,3-dioxane, as well as certain heavier polyamines. Interestingly, there appears to be no evidence for the formation of piperazine-type derivatives during this C-3 bridge amination.

By contrast, poor hydroamination of a 25% aqueous solution of 1,3-propanediol to 1,3-propanediamine was realized in ex. 12 and 13, using copper-rich and copper-cobalt catalysts of the prior art.

To illustrate the process of the invention, the following examples are given. It is understood, however, that the examples are given only in the way of illustration and are not to be regarded as limiting the invention in any way.

EXAMPLES

A 50 cc continuous upflow reactor was employed in examples 1 to 13. The reactor was charged with the various nickel or cobalt catalysts, which are identified in each chart. The 1,3-propanediol was introduced in about a 25% to 50% aqueous solution and excess ammonia and hydrogen was passed over the catalyst bed as it was heated to 160° C. The temperature was then gradually increased to about 220 to 240° C.

EXAMPLES 1–11

Examples 1–11 and Tables I through XI summarize data for the one-step process for making 1,3-propanediamine (1,3-PDA) from 1,3-propanediol. In these examples the catalyst identified in each chart was charged to the stainless-steel reactor system in an amount of 50 g, or more, as specified. The 1,3-propanediol was fed to said reactor upflow, as a 25% to 50% aqueous solution, unless otherwise specified, along with excess ammonia and controlled quantities of hydrogen. The ammonia/1,3-propanediol feed molar ratio was generally between 18 and 35. The hydrogen feed rate was 5 liters/hr. The ammonia plus 1,3-propanediol solution feed rate was 20–100 cc/hr. Operating pressure was 2300 psi. Effluent products were collected in stainless-steel bombs and analyzed by gc and gc-ms/ir techniques Solid catalysts shown to be effective 1,3-PDO amination catalysts in examples 1–11 include:

Raney cobalt catalyst with nickel and molybdenum promoters (ex. 1 and 2) in granular form.

Raney nickel catalysts (ex. 5) and Raney nickel with a molybdenum promoter (ex. 3, 4, and 10), also in granular form.

A nickel-rich, bulk-metal catalyst containing ca. 50% nickel and 1.8% molybdenum oxide (ex. 6, 8, and 9).

A Raney nickel catalyst in extruded form (ex. 1).

Much lower levels of 1,3- PDO amination were realized with a standard copper chromite catalyst (75% copper oxide)—see example 7.

Summary 1,3-PDA selectivity data are estimated in Table XII for the more active amination catalysts of examples 1–11, together with the corresponding 1,3-PDO conversion numbers.

TABLE 1

| | | | | | 1,3-PDO AMINATION | | | | | |
|---|---|---|---|---|---|---|---|---|---|---|
| EX. | CATALYST | TEMP. (° C.) | LHSV | SAMPLE (g) | CONC. (%) 1,3-PDO | CONC. (%) APO | CONC. (%) 1,3-PDA | CONC. (%) DPTA | CONC (%) TPTA | CONC. (%) (NH$_2$C$_3$) (HOC$_3$)$_2$NH |
| 23771-119 | Raney Co, Grace 48% Co + Ni/Mo,R-2786[a] | 160 | 1.0[a] | 94[b] | 72.3 | 16.1 | 4.9 | 0.9 | | 1.6 |
| | | | | | 59.5 | 13.8 | 4.0 | 0.6 | | 1.3 |
| | | 180 | 1.0[a] | 142[b] | 53.4 | 18.4 | 15.3 | 3.6 | | 4.5 |
| | | | | | 47.4 | 16.1 | 13.2 | 3.8 | | 3.9 |
| | | 200 | 1.0[a] | 105[b] | 25.0 | 11.5 | 32.6 | 12.1 | 2.9 | 3.7 |

TABLE 1-continued 1,3-PDO AMINATION

| EX. | CATALYST | TEMP. (° C.) | LHSV | SAMPLE (g) | CONC. (%) 1,3-PDO | CONC. (%) APO | CONC. (%) 1,3-PDA | CONC. (%) DPTA | CONC (%) TPTA | CONC. (%) ($NH_2C_3$) ($HOC_3)_2NH$ |
|---|---|---|---|---|---|---|---|---|---|---|
| | | | | | 22.0 | 11.0 | 32.2 | 11.0 | 3.1 | 3.4 |
| | | 220 | 1.0[a] | 134[b] | 11.1 | 5.7 | 31.4 | 7.5 | | 1.4 |
| | | | | | 11.1 | 5.8 | 32.2 | 7.4 | | 3.4 |

[a]Loaded with 50 g of Raney Co
[b]Feed, aqueous 25% 1,3-PDO + $NH_3$ (1:2 mix)

TABLE II 1,3-PDO AMINATION

| Ex. 2 | CATALYST | TEMP. (° C.) | LHSV | SAMPLE (g) | CONC. (%) 1,3-PDO | CONC. (%) APO | CONC. (%) 1,3-PDA | CONC. (%) DPTA | CONC. (%) TPTA | CONC. (%) ($NH_2C_3$) ($HOC_3)_2NH$ |
|---|---|---|---|---|---|---|---|---|---|---|
| 23771-121 | Raney Co, Grace 48% Co + Ni/Mo,R-2796[a] | 160 | 0.4[b] | 43 | 75.7 | 9.0 | 4.9 | 1.4 | | 2.9 |
| | | | | | 74.4 | 12.4 | 5.6 | 0.9 | | 2.4 |
| | | 180 | 0.4[b] | 50 | 52.0 | 12.6 | 10.5 | 6.8 | 3.8 | 6.8 |
| | | | | | 49.7 | 12.4 | 10.6 | 7.0 | 3.9 | 6.7 |
| | | 200 | 0.4[b] | 53 | 26.3 | 7.9 | 17.6 | 10.9 | 5.8 | 4.8 |
| | | | | | 24.0 | 8.4 | 20.3 | 9.9 | 4.8 | 4.2 |
| | | 220 | 0.4[b] | 69 | 17.9 | 5.7 | 19.2 | 7.0 | 3.0 | 2.4 |
| | | | | | 20.2 | 6.3 | 22.0 | 7.8 | 3.3 | 2.7 |
| | | 230 | 0.4[b] | 45 | 13.6 | 3.2 | 13.8 | 2.7 | | |
| | | | | | 16.3 | 4.6 | 18.9 | 3.2 | | |

[a]Loaded with 50 g of Raney Co
[b]Feed aqueous 50% 1,3-PDO + $NH_3$ (1:2 mix)

TABLE III 1,3-PDO AMINATION

| Ex. | CATALYST | TEMP. (° C.) | LHSV | SAMPLE (g) | CONC. (%) 1,3-PDO | CONC. (%) APO | CONC. (%) 1,3-PDA | CONC. (%) DPTA | CONC. (%) TPTA. | CONC. (%) ($NH_2C_3$) ($HOC_3)_2NH$ |
|---|---|---|---|---|---|---|---|---|---|---|
| 23771-127 | Raney Ni, Grace 55% Ni + Mo, R-3142[a] | 160 | 1.0[b] | 115 | 100.0 | 9.0 | | | | |
| | | | | | 96.0 | 12.4 | 1.4 | | | |
| | | 180 | 1.0[b] | 123 | 91.1 | 5.9 | 2.4 | | | |
| | | | | | 91.7 | 5.8 | 2.5 | | | |
| | | 200 | 1.0 | 51 | 70.6 | 14.7 | 14.7 | | | |
| | | | | | 64.7 | 13.6 | 14.7 | 2.3 | | |
| | | 220 | 1.0[b] | 57 | 39.3 | 13.6 | 28.6 | 5.9 | | 1.6 |
| | | | | | 35.8 | 13.3 | 29.1 | 5.2 | | 1.3 |
| | | 230 | 1.0[b] | 108 | 31.3 | 12.8 | 33.3 | 4.6 | | 1.1 |
| | | | | | 33.4 | 13.0 | 30.8 | 3.8 | | 1.1 |
| | | 240 | 1.0[b] | 138 | 24.6 | 11.7 | 28.9 | | | |
| | | | | | 22.2 | 11.3 | 27.9 | | | |

[a]Loaded with 50 g of Raney Ni
[b]Feed aqueous 25% 1,3-PDO + $NH_3$ (1:2 mix)

TABLE IV 1,3-PDO AMINATION

| Ex. 4 | CATALYST | TEMP. (° C.) | LHSV | SAMPLE (g) | CONC. (%) 1,3-PDO | CONC. (%) APO | CONC. (%) 1,3-PDA | CONC. (%) DPTA | CONC. (%) TPTA | CONC. (%) (NH$_2$C$_3$) (HOC$_3$)$_2$NH |
|---|---|---|---|---|---|---|---|---|---|---|
| 23771-131 | Raney Ni, Grace 55% Ni + Mo, R-3142[a] | 200 | 0.16[b] | 20 | 10.4 | 6.0 | 38.0 | 10.4 | | |
| | | | | | 9.9 | 5.0 | 36.8 | 9.7 | | |
| | | 220 | 0.16[b] | 36 | 3.3 | 1.9 | 21.1 | 2.9 | | |
| | | | | | 3.4 | 2.3 | 25.0 | 2.8 | | |
| | | 180 | 0.16[b] | 34 | 37.0 | 19.4 | 28.3 | 5.1 | | 1.2 |
| | | | | | 35.7 | 19.1 | 29.0 | 5.4 | | 1.8 |

[a]Reactor loaded with 124 g of Raney Ni
[b]Feed, aqueous 25% 1,3-PDO + NH$_3$ (1:2 mix)

TABLE V 1,3-PDO AMINATION

| Ex. 5 | CATALYST | TEMP. (° C.) | LHSV | SAMPLE (g) | CONC. (%) 1,3-PDO | CONC. (%) APO | CONC. (%) 1,3-PDA | CONC. (%) DPTA | CONC. (%) TPTA | CONC. (%) (NH$_2$C$_3$) (HOC$_3$)$_2$NH |
|---|---|---|---|---|---|---|---|---|---|---|
| 23771-133 | Raney Ni, Grace 52% Ni, R-5886[a] | 160 | 0.16[b] | 26 | 98.6 | | 0.6 | | | |
| | | | | | 100.0 | | | | | |
| | | 180 | 0.16[b] | 25 | 69.4 | 17.8 | 10.5 | 0.7 | | |
| | | | | | 67.3 | 18.5 | 11.8 | 0.6 | | |
| | | 200 | 0.16[b] | 41 | 35.2 | 15.2 | 32.7 | 7.0 | | 1.1 |
| | | | | | 29.5 | 13.5 | 29.3 | 6.6 | 1.5 | 1.8 |
| | | 220 | 0.16[b] | 43 | 16.5 | 7.2 | 32.0 | 5.7 | | |
| | | | | | 15.6 | 7.2 | 30.9 | 5.7 | | |
| | | 230 | 0.16[b] | 34 | 15.1 | 5.0 | 23.7 | | | |
| | | | | | 15.3 | 5.3 | 22.4 | | | |

[a]Reactor loaded with 125 g of Raney Ni
[b]Feed, aqueous 25% 1,3-PDO + NH$_3$ (1:2 mix)

TABLE VI 1,3-PDO AMINATION

| Ex. 6 | CATALYST | TEMP. (° C.) | LHSV | SAMPLE (g) | CONC. (%) 1,3-PDO | CONC. (%) APO | CONC. (%) 1,3-PDA | CONC. (%) DPTA | CONC. (%) TPTA. | CONC. (%) (NH$_2$C$_3$) (HOC$_3$)$_2$NH |
|---|---|---|---|---|---|---|---|---|---|---|
| 23771-139 | Ni - 3275, 1/32"E Engelhard[a] | 160 | 0.22[b] | 24 | 83.7 | 11.0 | 4.7 | | | |
| | | | | | 83.3 | 10.7 | 5.0 | | | |
| | | 180 | 0.22[b] | 41 | 37.1 | 15.7 | 31.3 | 7.2 | 0.6 | 1.7 |
| | | | | | 36.4 | 16.0 | 31.9 | 7.1 | 0.6 | 2.0 |
| | | 200 | 0.22[b] | 43 | 23.1 | 10.5 | 30.7 | 5.5 | | 1.5 |
| | | | | | 20.8 | 10.6 | 31.0 | 4.2 | | 0.9 |
| | | 220 | 0.22[b] | 40 | 13.7 | 6.8 | 14.5 | | | |
| | | | | | 15.6 | 7.6 | 18.1 | | | |

[a]Reactor loaded with 89 g of Ni catalyst
[b]Feed aqueous 25% 1,3-PDO + NH$_3$ (1:2 mix)

TABLE VII

1,3-PDO AMINATION

| Ex. 7 | CATALYST | TEMP. (° C.) | LHSV | SAMPLE (g) | CONC. (%) 1,3-PDO | CONC. (%) APO | CONC. (%) 1,3-PDA | CONC. (%) DPTA | CONC. (%) TPTA | CONC. (%) (NH$_2$C$_3$) (HOC$_3$)$_2$NH |
|---|---|---|---|---|---|---|---|---|---|---|
| 23771-141 | Cu-0203, 1/8" T Engelhard[a] | 160 | 0.19[b] | 40 | 98.6 100.0 | | | | | |
| | | 180 | 0.19[b] | 45 | 97.7 97.9 | | | 0.2 0.2 | | |
| | | 200 | 0.19[b] | 44 | 90.2 94.1 | 2.9 2.6 | 1.2 | | | |
| | | 220 | 0.19[b] | 31 | 74.1 76.3 | | 1.5 1.4 | | | |

[a]Reactor loaded with 103 g of Cu catalyst
[b]Feed aqueous 25% 1,3-PDO + NH$_3$(1:2 mix)

TABLE VIII

1,3-PDO AMINATION

| Ex. 8 | CATALYST | TEMP. (° C.) | LHSV | SAMPLE (g) | CONC. (%) 1,3-PDO | CONC. (%) APO | CONC. (%) 1,3-PDA | CONC. (%) DPTA | CONC. (%) TPTA | CONC. (%) (NH$_2$C$_3$) (HOC$_3$)$_2$NH |
|---|---|---|---|---|---|---|---|---|---|---|
| 23771-153 | Ni-3275, 1/32"E Engelhard[a] | 160 | 0.5[b] | 27 | 81.6 80.2 | 13.2 14.2 | 4.3 4.9 | | | |
| | | 180 | 0.5[b] | 104 | 48.5 48.5 | 22.1 22.1 | 23.0 23.0 | 3.0 3.0 | | 1.5 1.5 |
| | | 200 | 0.5[b] | 99 | 24.7 24.9 | 16.2 16.3 | 34.3 34.5 | 7.6 7.7 | 1.5 1.5 | 2.3 2.4 |
| | | 220 | 0.5[b] | 94 | 22.0 22.0 | 15.7 15.8 | 22.2 22.1 | 2.2 2.1 | | 1.1 |
| | | 230 | 0.5[b] | 57 | 32.9 32.8 | 19.6 19.5 | 16.4 16.2 | 1.1 1.1 | | 1.0 1.1 |

[a]Reactor loaded with 85 g of Ni catalyst
[b]Feed aqueous 25% 1,3-PDO + NH$_3$ (1:2 mix)

TABLE IX

1,3-PDO AMINATION

| Ex. 9 | CATALYST | TEMP. (° C.) | LHSV | TIME (DAYS) | SAMPLE (g) | CONC. (%) 1,3-PDO | CONC. (%) APO | CONC. (%) 1,3-PDA | CONC. (%) DPTA | CONC. (%) TPTA. | CONC. (%) (NH$_2$C$_3$) (HOC$_3$)$_2$NH |
|---|---|---|---|---|---|---|---|---|---|---|---|
| 23771-155 | Ni-3275, 1/32"E Engelhard[a] | 200 | 0.5[b] | 1 | 101 | 37.0 36.8 | 16.4 16.3 | 29.7 29.7 | 6.5 6.5 | 1.0 1.1 | 2.2 2.2 |
| | | 200 | 0.5[b] | 2 | 133 | 45.6 45.1 | 23.5 23.5 | 22.5 22.4 | 3.0 3.1 | | 1.8 2.0 |
| | | 200 | 0.5[b] | 3 | 124 | 54.4 54.3 | 24.5 24.5 | 15.5 15.5 | 1.4 1.4 | | 1.3 1.3 |
| | | 200 | 0.5[b] | 4 | 125 | 58.7 57.7 | 24.3 24.8 | 12.7 12.7 | 0.8 0.9 | | 0.9 1.1 |
| | | 200 | 0.5[b] | 5 | 91 | 63.3 63.7 | 23.1 23.4 | 9.6 9.7 | | | 0.8 0.8 |
| | | 220 | 0.5[b] | 6 | 112 | 43.3 42.8 | 23.4 23.2 | 14.1 14.0 | 1.3 1.2 | | 1.6 1.6 |
| | | 220 | 0.5[b] | 7 | 110 | 55..4 55.6 | 24.0 24.1 | 9.6 9.6 | | | 1.2 1.2 |
| | | 220 | 0.5[b] | 8 | 102 | 68.5 68.5 | 21.0 21.1 | 5.8 5.9 | | | |

[a]Reactor loaded with 82 g of Ni catalyst
[b]Feed aqueous 25% 1,3-PDO + NH$_3$ (1:2 mix)

TABLE X

1,3-PDO AMINATION

| Ex. 10 | CATALYST | TEMP. (°C.) | LHSV | SAMPLE (g) | CONC. (%) 1,3-PDO | CONC. (%) APO | CONC. (%) 1,3-PDA | CONC. (%) DPTA | CONC. (%) TPTA | CONC. (%) (NH$_2$C$_3$) (HOC$_3$)$_2$NH |
|---|---|---|---|---|---|---|---|---|---|---|
| 23771-161 | Raney Ni, Grace 60% Ni + Mo, R-3142[a] | 180 | 0.5[b] | 39 | 69.7 | 19.3 | 9.2 | | | |
| | | | | | 69.5 | 19.2 | 9.2 | | | |
| | | 200 | 0.5[b] | 162 | 30.0 | 16.5 | 32.7 | 9.3 | 2.2 | 2.5 |
| | | | | | 30.0 | 16.6 | 32.8 | 9.3 | 2.2 | 2.5 |
| | | 220 | 0.5[b] | 142 | 11.1 | 8.1 | 36.2 | 10.0 | 2.3 | 1.4 |
| | | | | | 11.2 | 8.1 | 36.2 | 9.9 | 2.4 | 1.4 |

[a]Reactor loaded with 125 g of Raney Ni catalyst
[b]Feed aqueous 25% 1,3-PDO + NH$_3$ (1:2 mix)

TABLE XI

1,3-PDO AMINATION

| Ex. 11 | CATALYST | TEMP. (°C.) | LHSV | SAMPLE (g) | CONC. (%) 1,3-PDO | CONC. (%) APO | CONC. (%) 1,3-PDA | CONC. (%) DPTA | CONC. (%) TPTA. | CONC. (%) (NH$_2$C$_3$) (HOC$_3$)$_2$NH |
|---|---|---|---|---|---|---|---|---|---|---|
| | Raney Ni, Grace 3/16"E[a] | 160 | 0.5[b] | 59 | 94.2 | 3.3 | 1.4 | | | |
| | | | | | 94.0 | 3.5 | 1.4 | | | |
| | | 180 | 0.5[b] | 75 | 83.9 | 11.2 | 3.3 | | | |
| | | | | | 83.6 | 11,1 | 3.1 | | | |
| | | 200 | 0.5[b] | 90 | 62.6 | 16.5 | 13.1 | 1.7 | | 1.0 |
| | | | | | 62.5 | 16.5 | 13.1 | 1.7 | | 1.0 |
| | | 220 | 0.5[b] | 99 | 41.1 | 11.7 | 23.9 | 4.3 | | 1.2 |
| | | | | | 40.8 | 11.6 | 23.8 | 4.3 | | 1.2 |
| | | 240 | 0.5[b] | 76 | 16.8 | 3.9 | 11.8 | | | |
| | | | | | 17.1 | 4.0 | 12.1 | | | |

[a]Reactor loaded with 88 g of Raney Ni catalyst
[b]Feed aqueous 25% PDO + NH$_3$ (1:2 mix)

TABLE XII

Table XII summarizes data regarding product amine selectivities and 1,3-PDO conversion levels for the 1,3-propanediol hydroamination examples 1–11

| EX. | CATALYST | TEMP.(°C.) | LHSV | CONV.(%) | AMINE SELECTIVITY(%) | | | |
|---|---|---|---|---|---|---|---|---|
| | | | | | 1,3-PDA | DPTA | TPTA | APO |
| 1 | Raney Co + Ni/Mo, R-2796 | 200 | 1.0 | 75 | 43 | 16 | 4 | 15 |
| 3 | Raney Ni + Mo, R3142 | 230 | 1.0 | 69 | 48 | 7 | <1 | 19 |
| 4 | " | 200 | 0.16 | 90 | 42 | 12 | 5 | 7 |
| 5 | Raney Ni, R-5886 | 200 | 0.16 | 65 | 50 | 11 | <1 | 23 |
| 6 | Engelhard Ni, 3275 | 180 | 0.22 | 64 | 50 | 12 | 1 | 25 |
| 8 | " | 200 | 0.5 | 75 | 46 | 10 | 2 | 22 |

COMPARATIVE EXAMPLES 12–13

Comparative examples 12 and 13 illustrate the one-step process for making 1,3-propanediamine from 1,3-propanediol either with a copper-rich (40–60% copper oxide) catalyst, or a copper-cobalt catalyst of the prior art. It may be seen from the data in Tables XIII and XIV that the effluent concentrations of 1,3-PDA in these examples were much lower than those reported for the catalysts of examples 1–11. These copper and copper-cobalt catalysts are judged to be poor choices for 1,3-PDO hydroamination.

TABLE XIII 1,3-PDO AMINATION - COMPARATIVE

| Ex. 12 | CATALYST | TEMP. (° C.) | LHSV | SAMPLE (g) | CONC. (%) 1,3-PDO | CONC. (%) APO | CONC. (%) 1,3-PDA | CONC. (%) DPTA | CONC. (%) TPTA | CONC. (%) (NH$_2$C$_3$) (HOC$_3$)$_2$NH |
|---|---|---|---|---|---|---|---|---|---|---|
| 23771-175 | Cu-0860, 1/8" T Engelhard[a] | 180 | 0.25[b] | 50 | 98.6 | | | | | |
| | | | | | 98.6 | | | | | |
| | | 200 | 0.25[b] | 52 | 92.8 | 1.8 | 1.0 | | | |
| | | | | | 91.0 | 1.9 | 1.0 | | | |
| | | 220 | 0.25[b] | 44 | 57.6 | 2.6 | 2.2 | 1.0 | | |
| | | | | | 58.1 | 2.6 | 2.2 | | | |

[a]Reactor loaded with 79 g of Cu catalyst
[b]Feed aqueous 25% PDO + NH$_3$ (1:2 mix)

TABLE XIV 1,3-PDO AMINATION - COMPARATIVE

| Ex. 13 | CATALYST | TEMP. (° C.) | LHSV | SAMPLE (g) | CONC. (%) 1,3-PDO | CONC. (%) APO | CONC. (%) 1,3-PDA | CONC. (%) DPTA | CONC. (%) TPTA | CONC. (%) (NH$_2$C$_3$) (HOC$_3$)$_2$NH |
|---|---|---|---|---|---|---|---|---|---|---|
| 23771-179 | L6540-6-1 Cu—Co, 1/32"E Engelhard[a] | 180 | 0.45[b] | 43 | 96.0 | 3.0 | | | | |
| | | | | | 96.1 | 2.9 | | | | |
| | | 200 | 0.45[b] | 50 | 78.6 | 12.8 | 4.8 | | | |
| | | | | | 78.5 | 13.0 | 4.9 | | | |
| | | 230 | 0.45[b] | 46 | 53.1 | 11.9 | 4.8 | | | |
| | | | | | 53.0 | 12.0 | 4.8 | | | |

[a]Reactor loaded with 44 g of Cu—Co catalyst
[b]Feed aqueous 25% 1,3-PDO + NH$_3$ (1:2 mix)

We claim:

1. A one-step process for the production of diaminoalkanes having two to six carbons which comprises: introducing into a reactor one or more $C_2$ to $C_6$ dihydric alcohols wherein the hydroxyl groups are separated by at least one carbon; reacting said $C_2$ to $C_6$ dihydric alcohol in the presence of excess ammonia and hydrogen and in the presence of a catalyst selected from the group consisting of Raney cobalt catalyst in granular form, Raney nickel catalyst in granular form, a nickel-rich, bulk-metal catalyst containing molybdenum oxide, and a Raney nickel catalyst in extruded form; reacting said $C_2$ to $C_6$ dihydric alcohol at a temperature of at least 150° C. and a pressure of at least 500 psi; and separating the diaminoalkane product.

2. The process of claim 1 wherein the dihydric alcohol is 1,3-propanediol and the product diaminoalkane is 1,3-propanediamine.

3. The process of claim 1 wherein the temperature range is from about 150° C. to about 250° C.

4. The process of claim 3 wherein the temperature range is from about 160° C. to 240° C.

5. The process of claim 4 wherein the temperature range is from about 180° C. to 220° C.

6. The process of claim 1 wherein the pressure is from about 500 psi to about 5000 psi.

7. The process of claim 6 wherein the pressure is from about 1000 psi to 3000 psi.

8. The process of claim 7 wherein the pressure is from about 2200 psi to 2500 psi.

9. The process of claim 2 further comprising introducing the 1,3-propanediol into the reactor in a solvent selected from the group consisting of alcohols, ethers and water.

10. The process of claim 9 wherein the 1,3-propanediol is introduced into the reactor in an aqueous solution of water.

11. The process of claim 2 wherein the one-step reaction can be represented by:

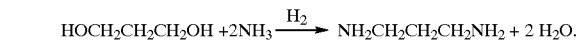

$$HOCH_2CH_2CH_2OH + 2NH_3 \xrightarrow{H_2} NH_2CH_2CH_2CH_2NH_2 + 2 H_2O. \quad (I)$$

12. The process of claim 2 wherein the molar ratio of ammonia to hydroxyl groups is 5-to 200:1.

13. The process of claim 2 wherein the hydrogen is fed to the reactor at a rate of 0.1–100 mole hydrogen/mole hydroxyl groups.

14. The process of claim 1 wherein the catalyst comprises on an oxide-free basis from about 10 to 95wt % nickel.

15. The process of claim 14 wherein the catalyst comprises on an oxide-free basis from about 50–60 wt % nickel.

16. The process of claim 14 further comprising the use of one or more promoters selected from the group consisting of Group VIII and Group VIB of the Periodic Table.

17. The process of claim 16 wherein the promoters are selected from the group consisting of nickel, cobalt, molybdenum, and chromium.

18. The process of claim 14 wherein the catalyst further comprises the use of a nickel catalyst with a molybdenum promoter.

19. The process of claim 1 wherein the catalyst contains on an oxide-free basis about 10–95% cobalt.

20. The process of claim 19 wherein the catalyst further comprises from about 10 to 80% cobalt, plus a nickel and molybdenum promoter.

21. The process of claim 19 wherein the catalyst comprises on an oxide-free basis from about 50 to 60% cobalt.

22. The process of claim 1 wherein the catalyst comprises at least one metal selected from the group consisting of nickel and cobalt as a bulk-metal catalyst.

23. The process of claim 22 wherein said bulk-metal catalyst contains 10 to 95 wt % nickel.

24. The process of claim 23 wherein said nickel-containing bulk-metal catalyst also contains a Group VIB metal.

25. The process of claim 24 wherein said Group VIB metal promoter is molybdenum.

26. The process of claim 25 wherein the molybdenum is present as molybdenum oxide.

27. The process of claim 26 wherein the molybdenum oxide content of said bulk-metal nickel catalyst is in the range of from 0.1 to 4 wt %.

28. The process of claim 1 wherein the catalyst comprises at least one metal selected from the group consisting of nickel and cobalt on a support.

29. The process of claim 28 wherein the support is selected from Groups II, III, IV, or V of the Periodic Table.

30. The process of claim 29 wherein the support is selected from the group consisting of magnesia, alumina, silica, zirconia, and titania, as well as mixtures thereof.

* * * * *